(12) United States Patent
McMullen et al.

(10) Patent No.: US 9,194,783 B2
(45) Date of Patent: Nov. 24, 2015

(54) ENDOSSEOUS DENTAL IMPLANT LOADING FIXTURE

(75) Inventors: Alan McMullen, Plymouth, MN (US);
Kristin M. McMullen, legal representative, Plymouth, MN (US);
Jason Lusk, Eagan, MN (US); Troy Nickel, Edina, MN (US)

(73) Assignee: TA INSTRUMENTS-WATERS L.L.C., Milford, MA (US)

( * ) Notice: Subject to any disclaimer, the term of this patent is extended or adjusted under 35 U.S.C. 154(b) by 352 days.

(21) Appl. No.: 13/592,873

(22) Filed: Aug. 23, 2012

(65) Prior Publication Data

US 2014/0053655 A1 Feb. 27, 2014

(51) Int. Cl.
| | | |
|---|---|---|
| *G01N 3/32* | (2006.01) | |
| *A61C 8/00* | (2006.01) | |
| *A61F 2/46* | (2006.01) | |
| *A61B 17/56* | (2006.01) | |
| A61C 19/04 | (2006.01) | |
| A61F 2/36 | (2006.01) | |

(52) U.S. Cl.
CPC *G01N 3/32* (2013.01); *A61B 17/56* (2013.01); *A61C 8/00* (2013.01); *A61F 2/468* (2013.01); A61C 19/04 (2013.01); A61F 2/36 (2013.01); Y10T 29/49826 (2015.01)

(58) Field of Classification Search
CPC .............. A61F 2/468; A61F 2/36; A61F 2/30; G01N 3/32; G01N 3/08; A61C 8/00; A61C 19/04; A61B 17/58
USPC ........... 73/821, 790, 798, 808, 810, 813, 814, 73/816, 818, 825
See application file for complete search history.

(56) References Cited

U.S. PATENT DOCUMENTS

| | | | | |
|---|---|---|---|---|
| 3,073,584 | A * | 1/1963 | Troeger | 267/160 |
| 5,014,719 | A * | 5/1991 | McLeod | 600/587 |
| 2004/0177701 | A1* | 9/2004 | Zubok et al. | 73/804 |
| 2005/0241404 | A1* | 11/2005 | Salvesen | 73/788 |
| 2007/0039400 | A1* | 2/2007 | Meyer et al. | 73/862.41 |
| 2011/0146385 | A1* | 6/2011 | Weinberg et al. | 73/37 |
| 2011/0223833 | A1* | 9/2011 | Rauscher et al. | 451/1 |

OTHER PUBLICATIONS

PDF of http://www.instron.us/wa/solutions/ISO-14801-Dental-Implant-Testing-in-Fluid-Bath.aspx? Nov. 26, 2011.*
PDF of http://flexpivots.com/flexural-pivot-products/ with picture dated Jan. 29, 2011.*
"Implants for surgery—Patial and total hip joint prostheses—Part 4: Determination of endurance properties and performance of stemmed femoral components." International Organization for Standardization (ISO), Jan. 15, 2008.
"Dentistry—Implants—Dynamic fatigue test for endosseous dental implants." International Organization for Standardization (ISO), Nov. 15, 2007.

* cited by examiner

*Primary Examiner* — Lisa Caputo
*Assistant Examiner* — Philip Cotey
(74) *Attorney, Agent, or Firm* — McCarter & English, LLP; Deborah M. Vernon

(57) ABSTRACT

An apparatus for fatigue testing an article includes a base having a platform for receiving an article to be tested, a shaft extending toward said platform for applying a force to said article, a coupling assembly connected to said shaft, said coupling assembly comprising a joint that pivots about an axis, and flex pivots disposed to be aligned with said axis about which said joint pivots.

13 Claims, 6 Drawing Sheets

Prior Art

ENDOSSEOUS DENTAL IMPLANT LOADING FIXTURE

FIELD OF DISCLOSURE

This disclosure relates to machines for fatigue testing of articles, and in particular, to machines for testing of endosseous dental implants.

BACKGROUND

One procedure for fatigue testing of dental implants includes having a loading shaft 10, shown in FIG. 1, repeatedly apply a compressive load to an implant 12. The direction of the force vector that applies the compressive load defines a load axis 14, as shown in FIG. 1.

During testing, the implant 12 is implanted into a mounting surface 16. A line that extends from the mounting surface to a point at which the force is applied defines a moment arm 18. To the extent the loading shaft 10, and hence the force vector, is not parallel to this moment arm 18, there will be a torque that urges the implant 12 to rotate or bend.

The extent to which the implant 12 resists such rotation or bending is of considerable interest. In fact, ISO 14801 describes a testing procedure and a fixture to be used for such a procedure. According to section 5.2.1 of that standard, the loading force is to be applied such that no lateral constraint occurs. According to section 5.2.6, the loading device should be unconstrained in the transverse direction so as to avoid reducing the magnitude of the applied torque. The standard further specifies that this should be accomplished by either providing a universal joint or by point contact between whatever applies the loading force and the implant 12.

The application of point contact is difficult, and when an implant 12 fails the test, the loading member falls away unless otherwise suspended.

Testing machines that rely on a universal joint to comply with the ISO standard are known. However, inherent in a conventional universal joint is a backlash that results from a delay between the time a drive motor applies a force and the time at which this force is actually transmitted down a shaft. This delay arises from slack in the bearings used in the pivots of a universal joint. In part as a result of this, universal joints require considerable maintenance. However, even with diligent maintenance, under the grueling test conditions of repeatedly applying a compressive load to an implant 12, such joints have a tendency to fail prematurely. In addition, the wear on these bearings results in a constant dispersal of small metal particles or shavings during use.

SUMMARY

The invention is based on the recognition that flexural pivots can be used to both comply with the requirements of the ISO and to achieve a backlash and maintenance free joint with essentially infinite lifetime.

In one aspect, the invention features an apparatus for fatigue testing an article. Such an apparatus includes a base having a platform for receiving an article to be tested, a shaft extending toward the platform for applying a force to the article, and a coupling assembly connected to the shaft. The coupling assembly comprises a joint that pivots about an axis, and flex pivots disposed to be aligned with the axis about which the joint.

In some embodiments, the flex pivot is configured to rigidly transmit an axial force.

In other embodiments, the base further includes a curved holder, and wherein the platform is mounted to slide along the curved holder thereby causing an angle between the shaft and the article to vary.

Also included are embodiments in which the shaft includes a distal tip having a contact face for loading the article, and wherein the contact face includes zirconia, those embodiments in which the shaft includes a distal tip having a contact face for loading the article, and wherein the contact face includes a material having a hardness between 1000 Hv and 8000 Hv, and those embodiments in which the shaft includes a distal tip having a contact face for loading the article, and wherein the contact face includes a material having a hardness between 1300 Hv and 8000 Hv.

In certain embodiments, the coupling assembly includes a first clevis, a second clevis, and a pivot block, and wherein the flex pivots pivotally couples the first clevis and the second clevis to the pivot block.

Also included among the many embodiments of the invention are those in which each of the flex pivots includes concentric cylinders having resilient webbing extending across the cylinders for applying a restoring force to urge the cylinders to maintain a relative position therebetween.

The apparatus is applicable to a variety of articles to be tested, such as articles that extend from an anchor point to a point where a load is to be applied. Among these are embodiments in which the platform is adapted to receive a dental implant, and those in which the platform is adapted to receive an orthopedic implant, such as, for example, a hip implant.

In yet other embodiments of the invention, the shaft is configured for backlash-free transmission of a compressive force against the article.

In another aspect of the invention, an apparatus for fatigue testing an article includes means for receiving an article to be tested, means for transmitting a compressive force to the article, means for coupling the means for transmitting a compressive force to an actuator, the means for coupling comprising flex pivots disposed to be aligned with an axis about which the means for coupling pivots.

In some embodiments, the means for coupling includes a first clevis, a second clevis, and a pivot block, and wherein the flex pivots pivotally couples the first clevis and the second clevis to the pivot block.

In another aspect of the invention, a method of making an apparatus for fatigue testing an article includes providing a base having a platform for receiving an article to be tested, providing a shaft extending toward the holder for applying a force to the article, connecting a coupling assembly to the shaft, the coupling assembly comprising a joint that pivots about an axis, and disposing flex pivots to be aligned with the axis about which the joint pivots.

Among the practices of the invention are those that also include providing the base with a curved holder, and mounting the platform to slide along the curved holder thereby causing an angle between the shaft and the article to vary.

Other practices also include providing the shaft with a distal tip having a contact face for applying a compressive load to the article, and selecting the contact face to comprise zirconia, or a material having a hardness between 8000 Hv and 1000 Hv, or a material having a hardness between 8000 Hv and 1000 Hv.

Yet other practices include providing the coupling assembly with a first clevis, a second clevis, and a pivot block, and wherein the flex pivots pivotally couples the first clevis and the second clevis to the pivot block.

In additional practices, the inventive method further includes providing each of the flex pivots with concentric cylinders having resilient webbing extending across the cylinders for applying a restoring force to urge the cylinders to maintain a relative position therebetween.

The manufacture of the apparatus can include customizing it for particular applications. For example, one practice includes adapting the platform to receive a dental implant, while another includes adapting the platform to receive an orthopedic implant, such as a hip implant.

In yet other practices, the shaft is configured for backlash-free transmission of a compressive force against the article.

These and other features of the invention will be apparent from the following description and its accompanying figures, in which:

DETAILED DESCRIPTION

Figure 1:
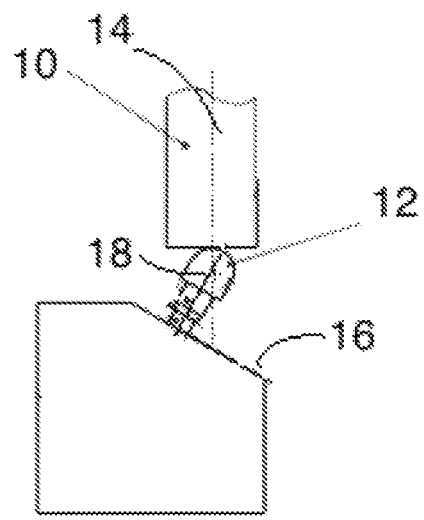
FIG. 1 shows a dental implant to be tested by a loading fixture.
Figure 2:
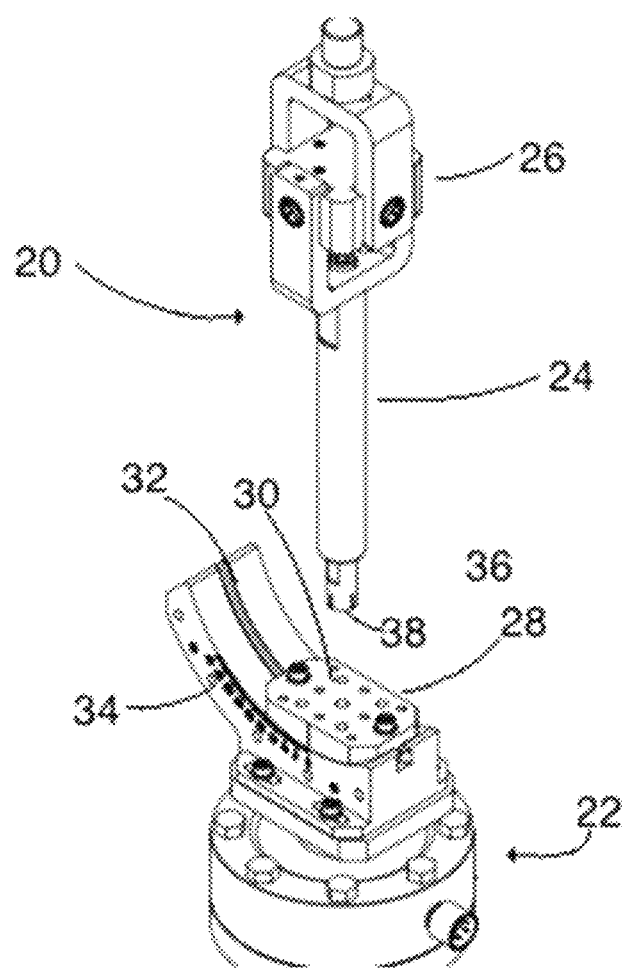
FIG. 2 shows an isometric view of a loading fixture for testing the dental implant shown in FIG. 1.

Referring to FIG. 2, a loading fixture 20 for fatigue testing of a dental implant 12 features a base 22, a shaft 24, and a coupling assembly 26 that couples the shaft 24 to an actuator (not shown).

The base 22 encloses various load sensors and features a platform 28 for receiving the dental implant 12 that is implanted into and protrudes from a top surface 30 thereof. This platform 28 engages a track 32 formed on a curved holder 34 such that the platform 28 can slide along the curved holder 34 along a range of angles. In doing so, a vector normal to the top surface 30 of the platform 28 defines a variable angle relative to a load axis defined by the shaft 24.

At a distal end 36 of the shaft 24 is a contact face 38 that contacts the dental implant 12 and transmits a load from the shaft 24 to the implant 12.

Figure 3:
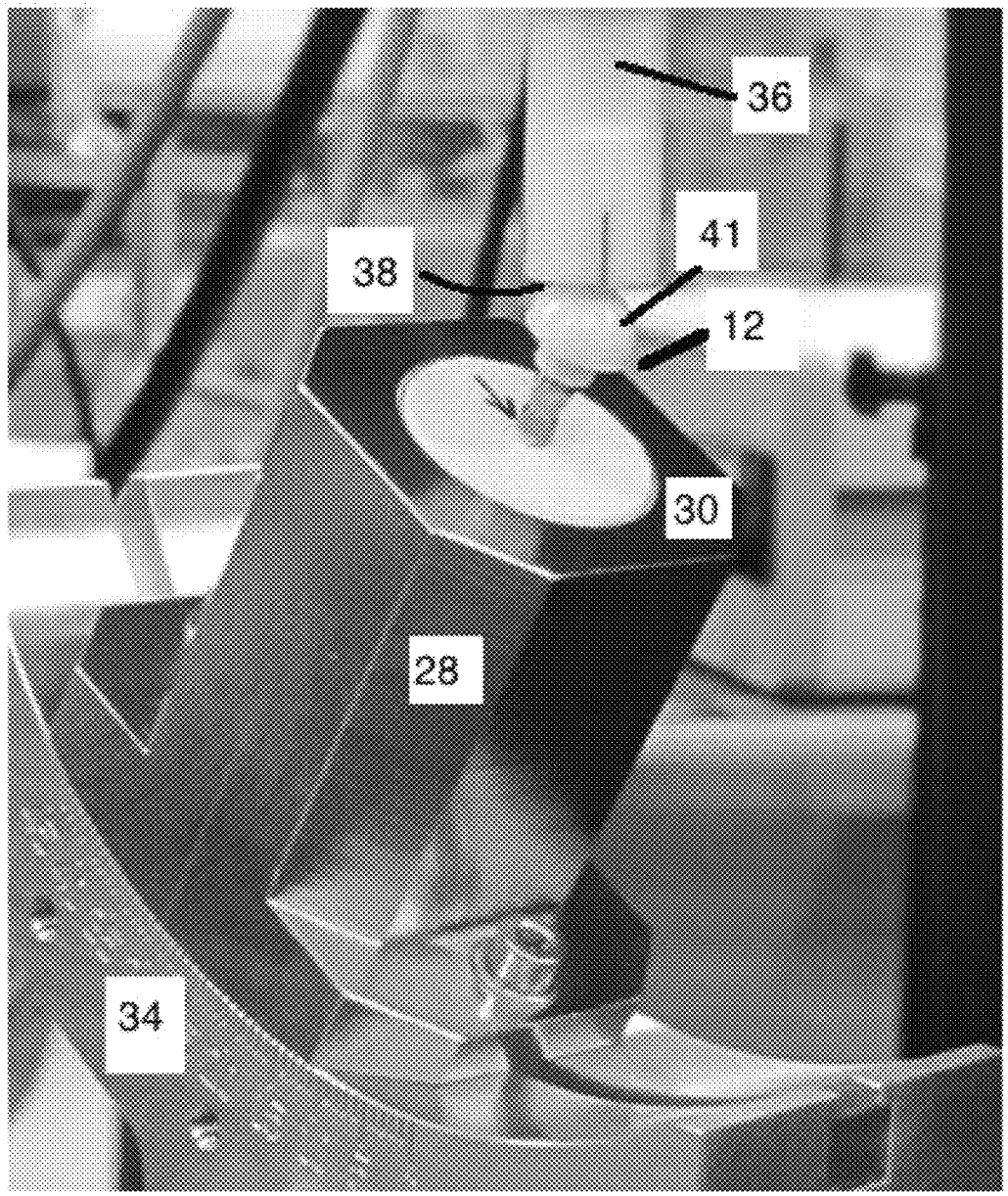
FIG. 3 shows a dental implant to be tested using the loading fixture of FIG. 2.

As shown in FIG. 3, a dental implant 40 typically has a hemispherical top surface 41 that receives repeated loading during a typical fatigue test. As a result, the force is concentrated on a small portion of the contact face 38. To avoid permanent deformation of the contact face 38 from repeated loading, it is useful to use a hard material for the contact face 38. Examples of such materials include, but are not limited to, hardened steel, diamond, and zirconia. Particularly useful materials have a hardness between 1000 Hv and 8000 Hv. Also useful for use on the contact face 38 are materials having a hardness between 1300 Hv and 8000 Hv.

Figure 4:
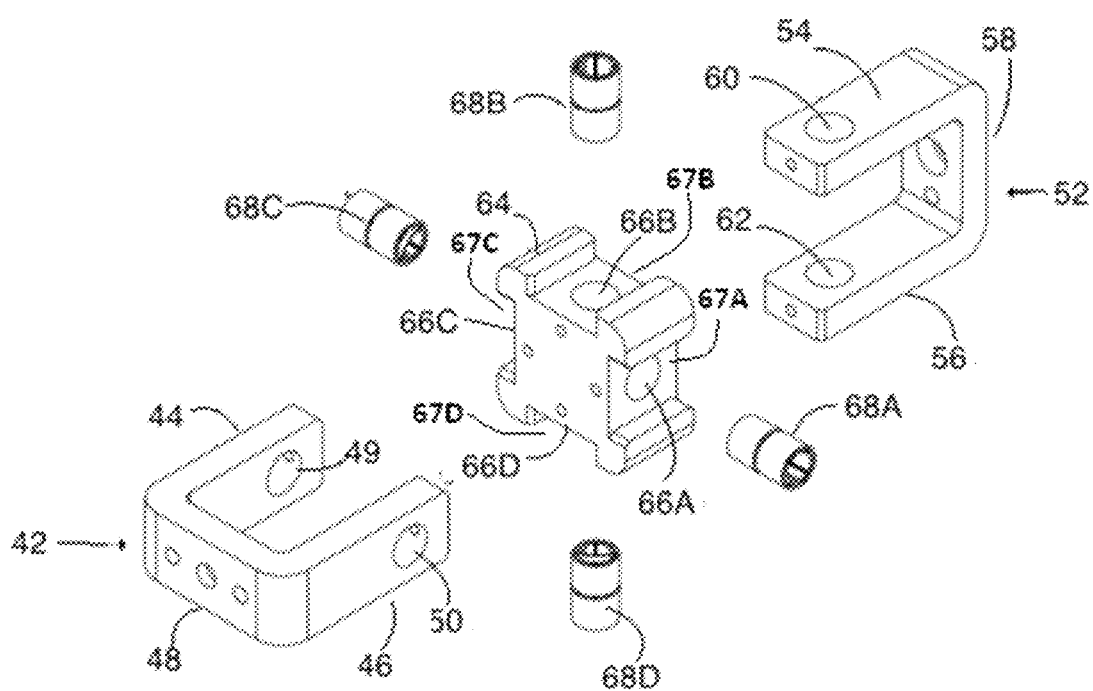
FIG. 4 shows the coupling assembly of the loading fixture of FIG. 2.

Referring now to FIG. 4, the coupling assembly 26 includes a first clevis 42 having first and second arms 44, 46 connected by a base 48. The distal ends of the first and second arms 44, 46 have through holes 49, 50 that are aligned with each other. The coupling assembly 26 also includes a second clevis 52 having first and second arms 54, 56 connected by a base 58, with through holes 60, 62 at the distal tips of the first and second arms 54, 56. As was the case in the first clevis 42, these through holes 60, 62 are also aligned with each other. The first and second clevises 42, 52 are orthogonal to each other such that a line normal to the first and second arms 44, 46 of the first clevis 42 is orthogonal to a line normal to the first and second arms 54, 56 of the second clevis 52.

The coupling assembly 26 also includes a pivot block 64 having a length and width chosen to fit between the first and second arms 44, 46 of the first clevis 42 and the first and second arms 54, 56 of the second clevis 52 respectively. A thickness of the pivot block 64 is chosen to accommodate recesses 66A-66D that are the same size and shape as the through-holes 48, 50, 60, 62 on the arms 44, 46, 54, 56 of the clevises 42, 52. When assembled, these through-holes 49, 50, 60, 62 align with corresponding recesses 66A-66D in the pivot block 64. Four flex pivots 68A-68D pass through corresponding through-holes 49, 50, 60, 62 and are secured into corresponding recesses in the pivot block 64.

A side of the pivot block 64 has a groove 67A for receiving a corresponding arm 46 of the first clevis 42. to accommodate one of the arms. A similar groove 67C is provided on an opposite side of the pivot block 64 to receive the opposite arm 44 of the first clevis 42. These grooves 67A, 67C cooperate to restrain the corresponding flex pivots 68A, 68C from rotating beyond their fatigue rated rotation angles as the first clevis 42 pivots about the pivot block 64. A similar pair of grooves 67B, 67D on the remaining two sides of the pivot block 64 cooperate to restrain the corresponding flex pivots 68B, 68D from rotating beyond their fatigue rated rotation angles as the second clevis 52 pivots about the pivot block 64.

As a result, the shaft 24 can pivot about a first rotational axis defined by first and third flex pivots 68A, 68C and a second rotational axis defined by second and fourth flex pivots 68B, 68D. This enables the application of a force without any constraint to motion in a lateral direction.

Figure 5:
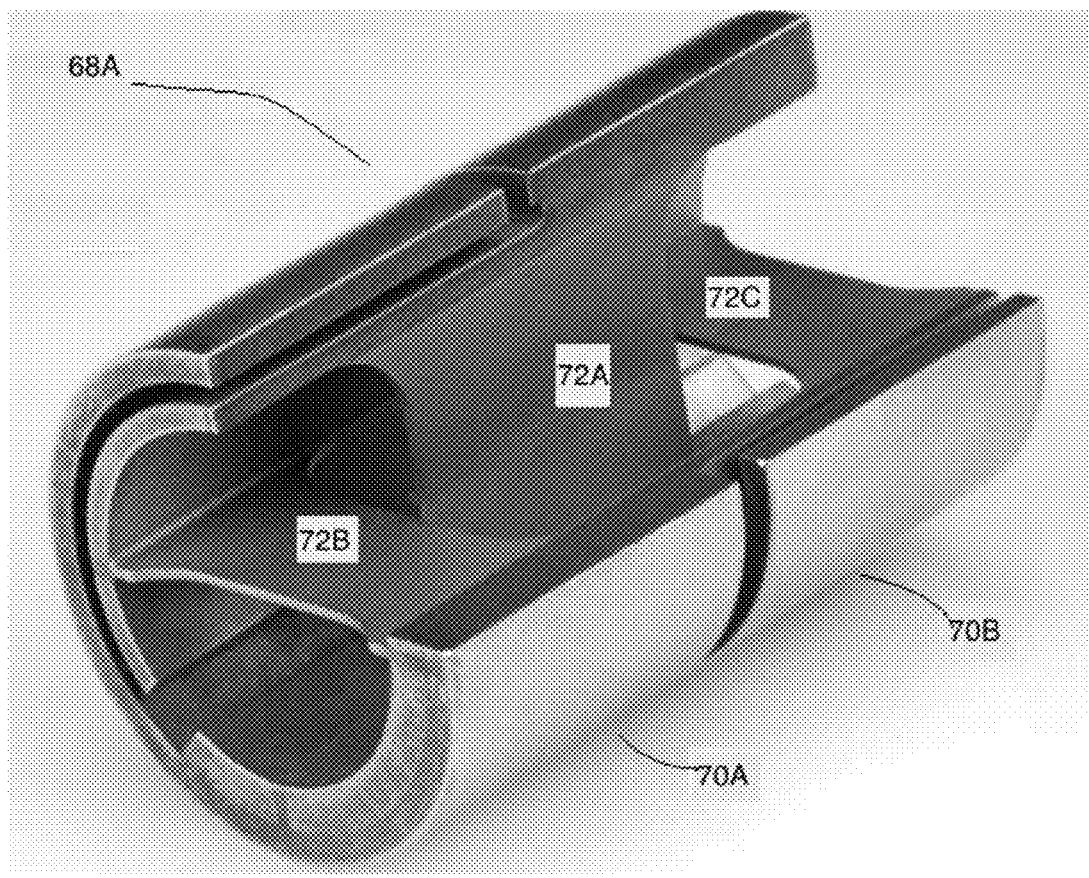
FIG. 5 shows a cut-away view of a flex pivot to be used with the coupling assembly shown in FIG. 4.

Referring now to FIG. 5, a typical flex pivot 68A includes two coaxial cylinders 70A, 70B adjacent to each other. A vertical web 72A extending across the diameter of the cylinders 70A, 70B joins them together. Horizontal webs 72B, 72C extend across the cylinders along a direction orthogonal to that of the vertical web 72A. The horizontal and vertical webs 72A, 72B, 72C thus cooperate to urge the cylinders 70A, 70B to remain collinear in response to any radial force and to provide a restoring force when the cylinders 70A, 70B are rotated relative to each other and.

Flex pivots 68A-68D as described herein are essentially frictionless devices that allow pivoting for limited angles. Such pivots 68A-68D do not require lubrication or maintenance and do not wear. As a result, such pivots 68A-68D do not cause fine metal dust or shavings to be formed during use.

An additional advantage of such flex pivots 68A-68D is the elimination of backlash. When flex pivots 68A-68D are used, there is no slack to be taken up as is the case when, for example, a ball bearing is used. A flex pivot 68A-68D eliminates the small but finite clearance in a ball bearing. Eliminating this clearance also eliminates the noise that results from backlash. As a result, when an actuator applies a force, the shaft 24 immediately and quietly transmits that force to the implant 12.

Preferably, the implant 12 experiences no lateral forces during testing. However, as the shaft 24 swings from side to side, at least some lateral force is inevitable. To minimize this lateral force, it is preferable to make the shaft 24 as long as possible.

When a shaft 24 of length l experiences an excursion of distance d as a result of pivoting about an angle $\theta$, the shaft 24 inevitably exerts a lateral force $F_{lat}$ that is equal to the axial force $F_{axial}$ weighted by the tangent of that angle $\theta$, i.e. $F_{lat}=F_{axial}\tan(\theta)$. Since the angle $\theta$ is the arcsine of the ratio of the excursion distance d to the length l, for a fixed excursion d, the longer the shaft 24 the lower the lateral force will be.

As described herein, the loading fixture 20 is used to test dental implants 12. However, the principles described herein are applicable to testing of any article subject to similar constraints.

Figure 6:
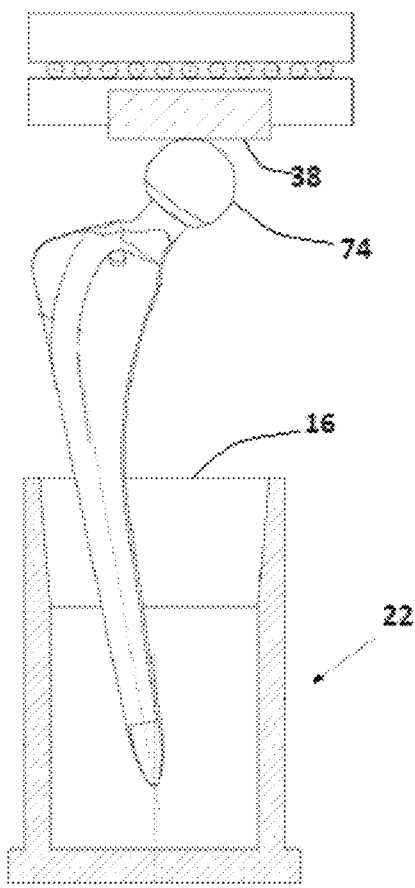
FIG. 6 shows a hip implant to be tested by a loading fixture.

In particular, the loading fixture 20 described herein can be used in a variety of applications in which one wishes to perform fatigue testing of a cantilevered article that is anchored at a point at some distance from where a compressive load is to be applied. For example, FIG. 6 shows a hip implant 74 anchored through a mounting surface 16 on a base 22. This hip implant 74 is to be fatigue tested by repeated application of a load from a contact face 38. A loading fixture 20 as described above can be adapted to perform fatigue testing of the hip implant 12.

Additional applications include testing of electronic components. For example, to test the integrity of solder joints connecting an integrated circuit to a circuit board, one might apply a loading force along a direction parallel to the circuit board. Or, in testing a composite material having an asymmetric distribution of fibers, it may be useful to apply a compressive force at some angle relative to the axis of the fibers to determine an extent to which bending or rotation may occur.

Having described the invention, and a preferred embodiment thereof, what we claim as new and secured by Letters Patent is:

1. An apparatus for fatigue testing an article, said apparatus comprising:
    a base having a platform for receiving an article to be tested,
    a shaft extending toward said platform for applying a force to said article,
    a coupling assembly connected to said shaft, said coupling assembly comprising a joint that pivots about an axis, and
    flex pivots aligned with said axis about which said joint pivots.

2. The apparatus of claim 1, wherein said flex pivot is configured to rigidly transmit an axial force.

3. The apparatus of claim 1, wherein said base further comprises a curved holder, and wherein said platform is mounted to slide along said curved holder thereby causing an angle between said shaft and said article to vary.

4. The apparatus of claim 1, wherein said shaft comprises a distal tip having a contact face for loading said article, and wherein said contact face comprises zirconia.

5. The apparatus of claim 1, wherein said shaft comprises a distal tip having a contact face for loading said article, and wherein said contact face comprises a material having a hardness between 1000 Hv and 8000 Hv.

6. The apparatus of claim 1, wherein said shaft comprises a distal tip having a contact face for loading said article, and wherein said contact face comprises a material having a hardness between 1000 Hv and 8000 Hv.

7. The apparatus of claim 1, wherein said coupling assembly comprises a first clevis, a second clevis, and a pivot block, and wherein said flex pivots pivotally couples said first clevis and said second clevis to said pivot block.

8. The apparatus of claim 1, wherein each of said flex pivots comprises concentric cylinders having resilient webbing extending across said cylinders for applying a restoring force to urge said cylinders to maintain a relative position therebetween.

9. The apparatus of claim 1, wherein said platform can receive a dental implant.

10. The apparatus of claim 1, wherein said platform can receive an orthopedic implant.

11. The apparatus of claim 1, wherein said shaft is configured for backlash-free transmission of a compressive force against said article.

12. An apparatus for fatigue testing an article, said apparatus comprising:
    means for receiving an article to be tested,
    means for transmitting a compressive force to said article,
    means for coupling said means for transmitting a compressive force to an actuator, said means for coupling comprising flex pivots aligned with an axis about which said means for coupling pivots to apply a restoring force in response to pivot of said joint.

13. The apparatus of claim 12, wherein said means for coupling comprises a first clevis, a second clevis, and a pivot block, and wherein said flex pivots pivotally couples said first clevis and said second clevis to said pivot block.

* * * * *